(12) United States Patent
Patel

(10) Patent No.: US 8,414,931 B2
(45) Date of Patent: Apr. 9, 2013

(54) MICRONIZED COPPER-CONTAINING COMPOSITIONS USEFUL TO MITIGATE RESIDUES ON WOOD SURFACES

(75) Inventor: Jayesh P. Patel, Stone Mountain, GA (US)

(73) Assignee: Arch Wood Protection, Inc., Atlanta, GA (US)

( * ) Notice: Subject to any disclaimer, the term of this patent is extended or adjusted under 35 U.S.C. 154(b) by 0 days.

(21) Appl. No.: 13/573,402

(22) Filed: Sep. 13, 2012

(65) Prior Publication Data
US 2013/0017271 A1 Jan. 17, 2013

Related U.S. Application Data

(62) Division of application No. 12/378,203, filed on Feb. 11, 2009, now Pat. No. 8,293, 282.

(60) Provisional application No. 61/065,516, filed on Feb. 12, 2008.

(51) Int. Cl.
| | |
|---|---|
| A01N 59/20 | (2006.01) |
| A01N 43/00 | (2006.01) |
| A01N 55/02 | (2006.01) |
| C09K 15/02 | (2006.01) |
| C09K 15/30 | (2006.01) |
| C09D 5/16 | (2006.01) |
| C08L 89/00 | (2006.01) |
| B05D 1/18 | (2006.01) |

(52) U.S. Cl.
USPC ........... 424/638; 424/630; 424/632; 424/633; 424/634; 424/635; 252/380; 252/389.53; 252/400.53; 106/15.05; 106/18.32; 514/383; 514/396; 514/499; 514/500; 514/642; 514/643

(58) Field of Classification Search .................. 424/638, 424/DIG. 11, 630, 632, 633, 634, 635, 637; 514/383, 396, 99, 500, 642, 643; 106/15.05, 106/18.32; 252/380, 389.53, 400.53
See application file for complete search history.

(56) References Cited

U.S. PATENT DOCUMENTS

| | | | | |
|---|---|---|---|---|
| 5,527,384 | A | * | 6/1996 | Williams et al. ........... 106/18.32 |
| 5,635,217 | A | * | 6/1997 | Goettsche et al. ........... 424/632 |
| 6,489,037 | B1 | * | 12/2002 | Winterowd et al. .......... 428/511 |
| 7,252,706 | B2 | | 8/2007 | Richardson et al. |
| 7,273,944 | B2 | | 9/2007 | Pasek et al. |
| 2004/0258767 | A1 | * | 12/2004 | Leach et al. .................. 424/630 |
| 2004/0258768 | A1 | | 12/2004 | Richardson et al. |
| 2005/0118280 | A1 | * | 6/2005 | Leach et al. .................. 424/617 |
| 2005/0171369 | A1 | * | 8/2005 | Pasek et al. ................... 556/113 |
| 2005/0252408 | A1 | * | 11/2005 | Richardson et al. ....... 106/15.05 |
| 2005/0255251 | A1 | | 11/2005 | Hodge et al. |
| 2006/0062926 | A1 | | 3/2006 | Richardson et al. |

(Continued)

*Primary Examiner* — Joseph D Anthony
(74) *Attorney, Agent, or Firm* — Lucas & Mercanti, LLP

(57) ABSTRACT

Disclosed is a wood preservative composition comprising micronized copper and copper-amine complex, wherein the copper component of the copper amine complex is from about 5% to about 50% by weight, based upon the total weight of copper in the composition. The copper amine complex serves to avoid wood surface "chalking" that is otherwise attributable to the presence of micronized copper in copper-based slurries used to treat wood products. In addition, the copper-amine complex enhances the antimicrobial efficacy of the composition when used in wood treatment applications by facilitating cell wall penetration of the treated wood.

5 Claims, 2 Drawing Sheets
(2 of 2 Drawing Sheet(s) Filed in Color)

U.S. PATENT DOCUMENTS

| | | |
|---|---|---|
| 2006/0078686 A1* | 4/2006 | Hodge et al. .................. 427/440 |
| 2006/0086284 A1 | 4/2006 | Zhang et al. |
| 2006/0288904 A1* | 12/2006 | Leach et al. ............... 106/15.05 |
| 2007/0193473 A1* | 8/2007 | Zhang et al. .............. 106/15.05 |
| 2008/0011201 A1 | 1/2008 | Strachan et al. |
| 2008/0072791 A1* | 3/2008 | Ashmore et al. ......... 106/287.18 |
| 2008/0199525 A1* | 8/2008 | Leach et al. .................. 424/489 |
| 2009/0123505 A1* | 5/2009 | Richardson et al. .......... 424/405 |
| 2009/0162410 A1* | 6/2009 | Zhang et al. .................. 424/409 |
| 2009/0203643 A1* | 8/2009 | Patel ............................... 514/55 |
| 2009/0223408 A1* | 9/2009 | Richardson et al. ......... 106/18.3 |
| 2009/0293761 A1* | 12/2009 | Richardson et al. ............ 106/18 |

* cited by examiner

Figure 1. Surface of Boards Treated Without and With C-9 and MEA Additives (Board Set 1)
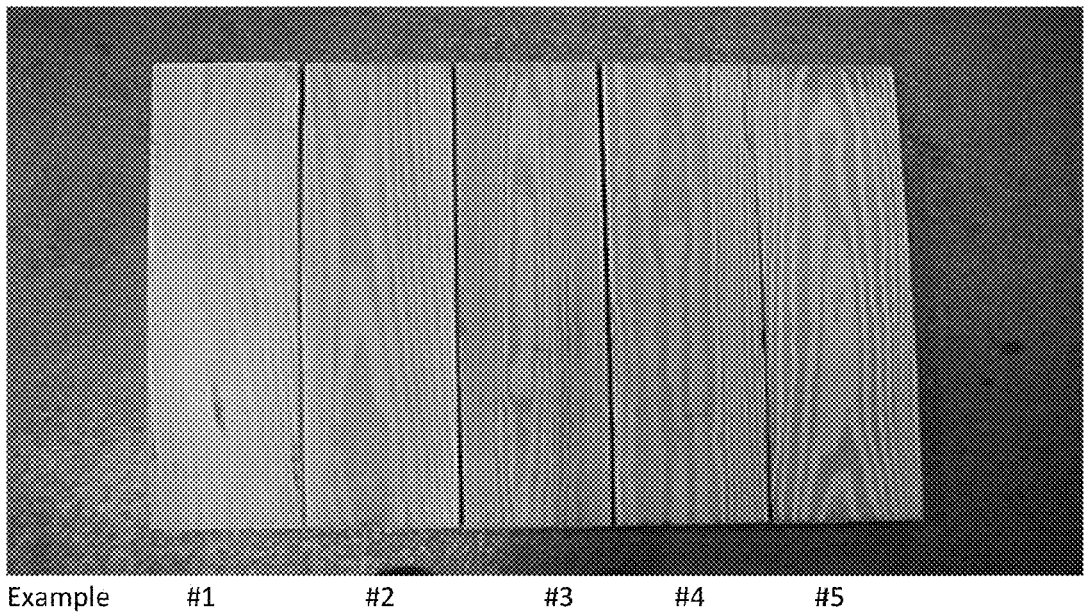
Example    #1        #2        #3        #4        #5
Figure 2. S Surface of Boards Treated Without and With C-9 and MEA Additives (Board Set 2)
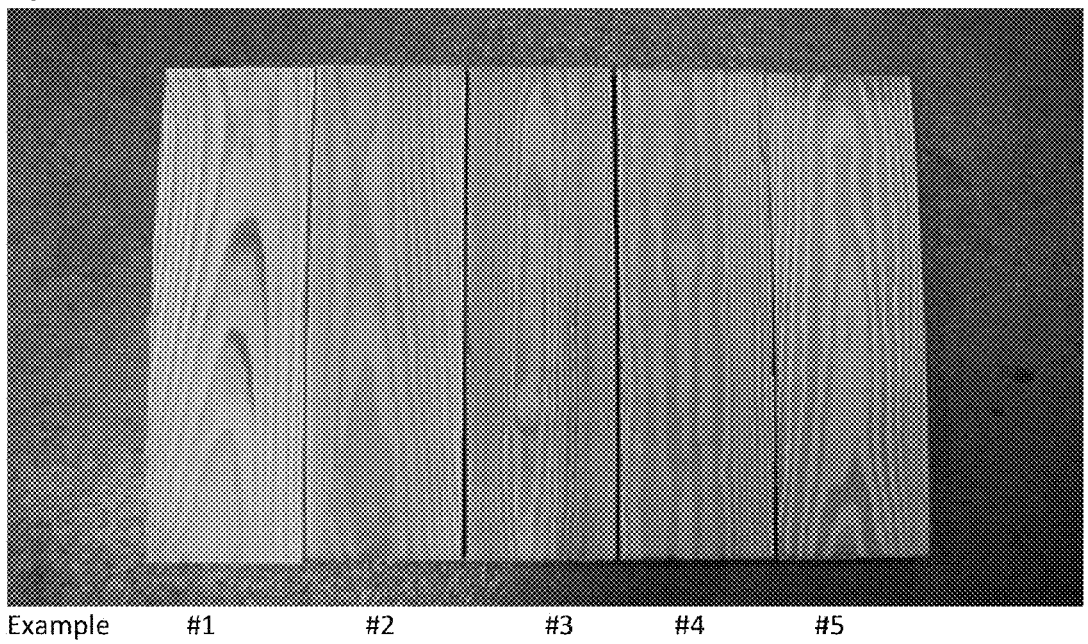
Example    #1        #2        #3        #4        #5

Fig. 3 Cumulative copper leach results for MCA-C at 0.05 pcf retention
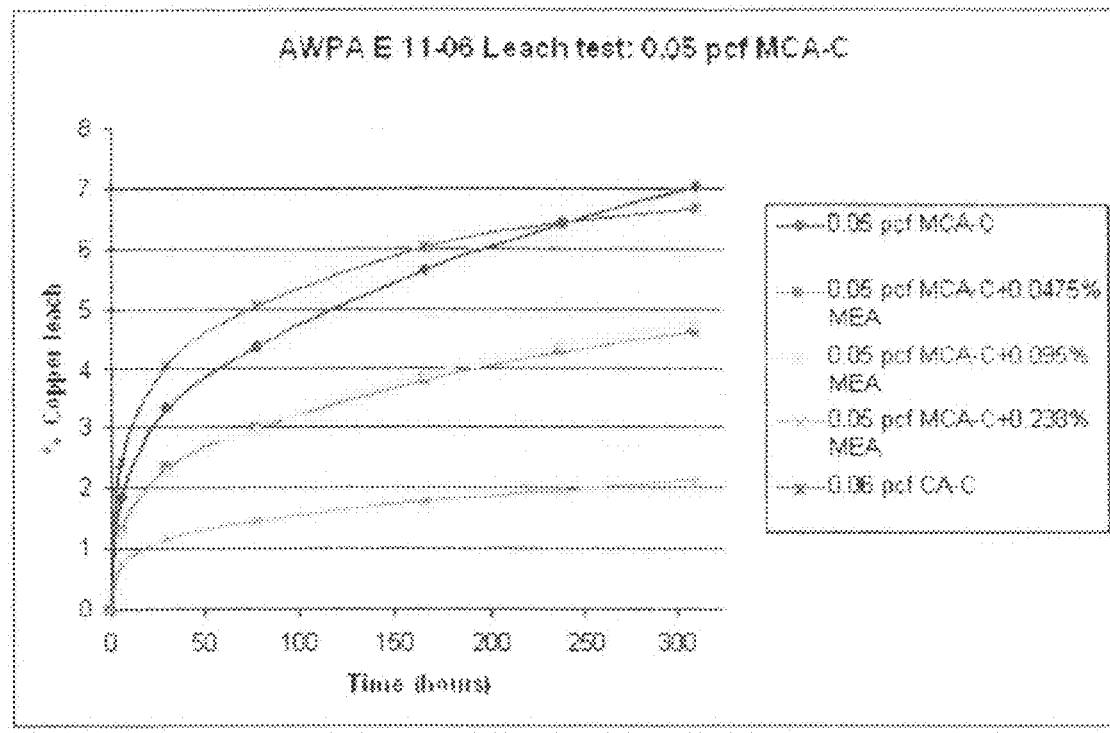
Fig. 4 Cumulative copper leach results for MCA-C at 0.14 pcf retention
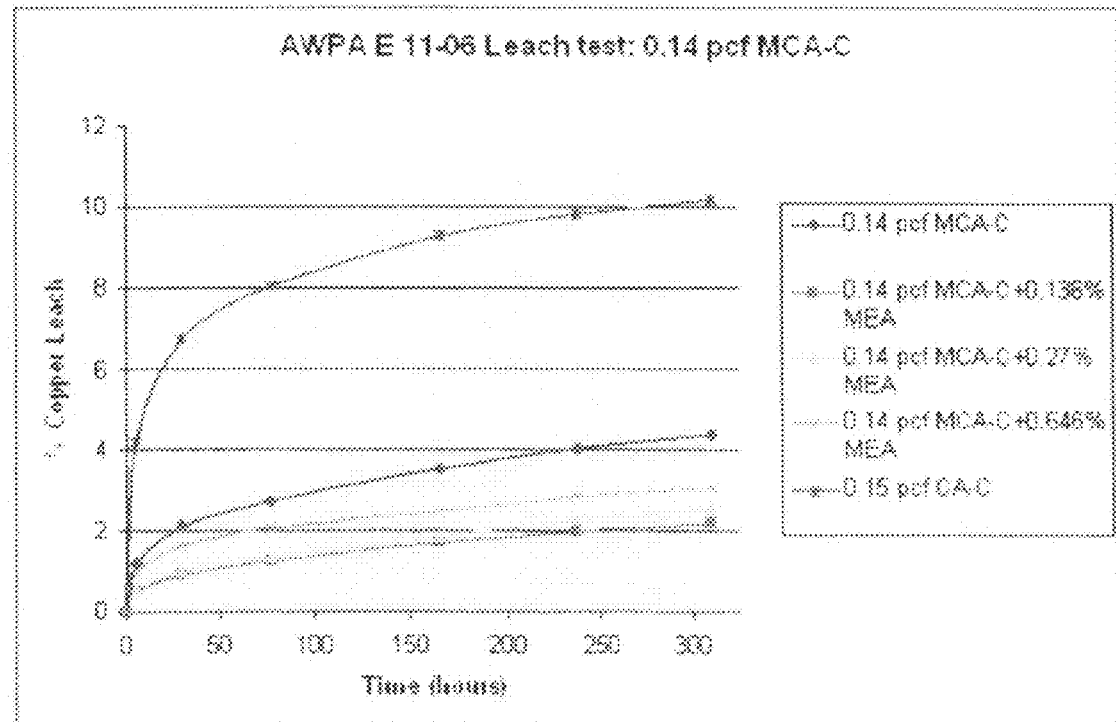

MICRONIZED COPPER-CONTAINING COMPOSITIONS USEFUL TO MITIGATE RESIDUES ON WOOD SURFACES

CROSS-REFERENCE TO RELATED APPLICATIONS

This patent application is a Division of U.S. patent application Ser. No. 12/378,203, filed Feb. 11, 2009 now U.S. Pat. No. 8,293,282, which claims the benefit of U.S. Provisional Application No. 61/065,516, filed Feb. 12, 2008. The disclosures of both applications are herein incorporated by reference.

FIELD OF INVENTION

The present invention relates to wood preservatives, particularly a wood preservative composition comprising micronized copper in particulate form, and copper-amine complex, wherein the copper component of the copper amine complex is from about 5% to about 50% by weight, based upon the total weight of copper in the composition. The invention also relates to a method for avoiding wood surface "chalking" that is otherwise attributable to the presence of micronized copper in copper-based slurries used to treat wood products.

BACKGROUND OF THE INVENTION

Wood preservatives are commonly used to protect wood from fungal and insect attack. Chromated copper arsenate (CCA) was used as a wood preservative from the mid-1930's until recent times. Recently, concerns were raised about safety and health effects of CCA and its use was voluntary discontinued for residential applications in 2002. Since this time, the US wood preservation industry focused primarily on the use of water-soluble, copper based preservatives.

The soluble copper based preservatives are aqueous solutions that contain soluble copper in the form of a copper-amine complex, a copper alkanolamine complex, or a copper ammonium complex. The soluble copper based preservatives typically contain at least one additional co-biocide in order to protect the wood from various copper tolerant brown rot fungi. Exemplary commercial formulations are Copper Azole (CA), Ammonical Copper Quat (ACQ), Copper HDO (CX) and Copper Naphthenate (CuN—W). However, the rising costs of alkanolamines coupled with relatively high water leachability of soluble copper from the treated wood products have resulted in a need in the industry for alternatives to soluble copper based wood preservatives.

One alternative to the use of water-soluble copper is to use copper in an insoluble form, such as in the form of submicron or micronized particles. Illustratively, U.S. Patent Applications 2006/0062926, 2005/0255251 and 2004/0258768, the disclosures of which are incorporated herein by reference in their entireties, describe methodology for making submicron-sized biocidal particulate slurries, such as particulate copper slurries, and their use as wood preservatives.

Although micronized copper wood preservatives provide a less expensive and a less leachable alternative to the use of soluble copper, it has now been found that using micronized copper to treat wood has a significant drawback. Specifically, the surface of the wood tends to exhibit an undesirable "chalky" appearance. As used herein, the term "chalky" refers to a powdery green residue appearing on the surface of treated wood. This chalking phenomenon is particularly exacerbated in certain areas of the treated wood surface, such as the heartwood portions that lack sufficient pore structure to allow penetration of the micronized copper particles into the wood, resulting in a "blotchy" uneven appearance of residue on the surface of the treated wood.

Certain compositions containing insoluble copper particulates and amines have been disclosed in the art. Illustratively, published U.S. application 2004/0258768 claims in claim 64 thereof a composition comprising a plurality of first particulates comprising at least 20% of a sparingly soluble copper salt suspended in an aqueous carrier comprising less than 1% by weight of alkanolamines and less than 1% by weight of ammonia. Paragraph 0170 of this publication discloses a slurry comprising a liquid carrier; injectable solid particulates comprising one or more organic biocides; and one or more soluble copper salts or complexes including the soluble copper treatments described in the prior art. Paragraph 0195 of this publication discloses such a liquid carrier comprising soluble copper, such as for example copper monoethanolamine carbonate complex.

Likewise, published U.S. application 2006/0062926 discloses a wood preservative slurry containing particles of a sparingly soluble copper salt. Paragraph 0115 of that publication discloses that the slurry can additionally comprise soluble copper-amine compounds, such as ammoniacal copper, copper-monoethanolamine complex, or a copper ethylenediamine complex; however, care should be taken to insure that the pH of the slurry does not approach the range where copper amine may precipitate, e.g. at about 7.5 or at about pH 13.

Although the problem of chalking associated with micronized copper treatment of wood has now been recognized, the art doesn't disclose or suggest any means to avoid it, to the knowledge of the present inventor. The present invention provides one solution to the problem.

SUMMARY OF THE INVENTION

In one aspect, the present invention relates to a wood preservative composition that exhibits the relative inexpensiveness and low leachability of micronized copper slurries, as compared to water-soluble copper solutions, while avoiding the surface chalking problem associated with micronized copper slurries that do not contain at least one nitrogen base or copper-amine complex. As used herein, the term "micronized" refers to material in particulate form having a particle size distribution such that the particle diameter of at least ninety five percent of the particles is within a range of from about 0.05 micron to about 1.5 microns. The composition of the present invention comprises micronized copper, and copper-amine complex, wherein the copper component of the copper amine complex is from about 5% to about 50% by weight, based upon the total weight of copper in the composition. The presence of the copper amine complex serves to enhance the antimicrobial efficacy of the composition by facilitating cell-wall penetration within the wood treated with the composition.

In another aspect, the present invention relates to a process for producing the above-mentioned wood preservative composition which comprises contacting an aqueous slurry of micronized copper with an additive selected from the group consisting of a copper-amine complex, a nitrogen base, and combinations thereof. The nitrogen base is selected from the group consisting of ammonia, alkylamines, arylamines, hydroxyalkylamines, alkyldiamines, and combinations thereof.

In still another aspect, the present invention relates to an improved method for avoiding a chalking appearance on the surface of treated wood, that is otherwise associated with particulate copper residues, the improvement comprising treating wood with a composition comprising micronized copper and copper-amine complex, wherein the copper component of the copper amine complex is present in an amount of from about 5% to about 50% by weight, based upon the total weight of copper in the composition.

In yet another aspect, the present invention relates to a stable wood preservative composition comprising micronized copper, a liquid carrier and a dispersing agent selected from the group consisting of a polycarboxylic acid or salt thereof, a lignosulfonic acid or salt thereof, and combinations thereof, in respective proportions effective to provide a stable slurry. The composition optionally further contains a copper-amine complex, wherein the copper component of the copper amine complex is from about 5% to about 50% by weight, based upon the total weight of copper in the composition.

These and other aspects will become apparent upon reading the detailed description of the invention.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 1 is a photograph showing a surface of boards treated without and with C-9 and MEA additives (board set #1).

FIG. 2 is a photograph showing a surface of boards treated without and with C-9 and MEA additives (board set #2).

FIG. 3 is a graph depicting leach rates over time for several compositions of the present invention, as compared to the leach rate for micronized copper without copper amine complex, and for copper amine complex without micronized copper.

FIG. 4 is a graph depicting leach rates over time for several compositions of the present invention, as compared to the leach rate for micronized copper without copper amine complex, and for copper amine complex without micronized copper.

DETAILED DESCRIPTION OF THE PREFERRED EMBODIMENTS

The wood preservative composition comprises micronized copper and copper-amine complex, wherein the copper component of the copper amine complex is from about 5% to about 50% by weight, based upon the total weight of copper in the composition. The presence of copper amine complex within this range of amounts serves to avoid wood surface "chalking" that otherwise results from the use of particulate copper in copper-based slurries to treat wood products. The copper-amine complex also serves to enhance the antimicrobial efficacy of the wood preservative composition by facilitating cell wall penetration of the treated wood.

Furthermore, it has now been surprisingly found that the composition of the present invention exhibits reduced leaching from wood treated with it, as compared to the amount of leaching associated with compositions containing either micronized copper without copper amine complex, or copper amine complex without micronized copper. Reduced leaching translates to sustained antimicrobial efficacy in the treated wood.

In one embodiment, the composition is suitably prepared by combining a micronized copper based slurry, and at least one additive selected from the group consisting of: a copper-amine complex, a nitrogen base, and combinations thereof.

The micronized copper based slurry is suitably prepared by using conventional grinding methodology, or other means known in the small particle production industry. The slurry comprises one or more of micronized element copper or copper containing compounds and a liquid carrier medium, such as water or an organic solvent in which the micronized copper is insoluble. The exemplary copper containing compounds include copper carbonates, copper oxides, copper hydroxides, copper chlorides, copper aromatic or aliphatic carboxylates, copper aminocarboxylates, and combinations thereof. The copper containing compound can also be any other suitable copper compounds known to those skilled in the art.

The insoluble copper particles in the copper-based slurry typically have a size such that wherein at least 95% of the particles have a particle diameter of from about 0.05 to about 1.5 microns, preferably from about 0.05 to about 1 micron, and most preferably from about 0.05 to about 0.7 microns.

The copper-amine complex is generally water soluble. This complex can be prepared by a variety of methods known to those skilled in the art, such as by the process disclosed in U.S. Pat. No. 7,273,944, the disclosure of which is incorporated herein by reference in its entirety. Suitably, the weight ratio of the elemental copper in the copper-amine complex relative to the elemental copper in the copper-based slurry is in the range of from about 0.02 to about 0.2.

Illustratively, the copper employed in producing the copper-amine complex in accordance with the present invention can be selected from elemental copper, copper carbonates, copper oxides, copper hydroxides, copper chlorides, copper aromatic or aliphatic carboxylates, and copper aminocarboxylates, and combinations thereof.

Illustratively, the amines employed in the copper amine complex in accordance with the present invention can be provided by ammonia or organo-amines, such as alkylamines, arylamines, hydroxyalkylamines, alkyldiamines, or combinations thereof. In a preferred embodiment, the amine is an ethanolamine, preferably monoethanolamine.

The weight ratio of copper to the amine in the copper-amine complex is between 1.0:2.5 and 1.0:5.0, preferably between 1.0:3.3 and 1.0:3.5. The weight ratio of the elemental copper in the copper-amine complex relative to the elemental copper in the copper-based slurry is in the range of from about 0.02 to about 0.2, preferably from about 0.1 to about 0.2.

In another embodiment, the present invention relates to a wooed preservative composition comprising one or more nitrogen bases and a micronized copper based slurry. The composition may suitably be prepared by combining a micronized copper-based slurry, and one or more nitrogen bases.

The micronized copper based slurry is as described above.

The nitrogen base(s) used in the present invention can be selected from ammonia or organo-amines, such as alkylamines, arylamines, hydroxyalkylamines, alkyldiamines, or combinations thereof. The preferred nitrogen base is the class of ethanolamines. The more preferred nitrogen base is monoethanolamine.

The nitrogen base may be present in the composition in an amount of from about 17% to about 170%, preferably from about 17% to about 102%, most preferably from about 17% to about 70%, based on the weight of copper in the micronized copper-based slurry.

The wood preservative composition can also be suitably prepared from a concentrate, such as a nitrogen base-containing micronized copper concentrate. The concentrate advantageously contains micronized copper, a nitrogen base and a liquid carrier, such as water, wherein the liquid carrier is present in an amount of less than 40%, preferably less than 20%, based upon the total weight of the concentrate. The nitrogen base may be present in an amount of from about 17% to about 170%, preferably from about 17% to about 102%, most preferably from about 17% to about 70%, based on the weight of elemental copper in the micronized copper component. The micronized copper may be present in an amount of from about 10% to 60%, preferably from about 20% to about 50%, based upon the total weight of the concentrate. The concentrate may additionally contain a soluble copper in the form of a copper-nitrogen base complex and a dispersing agent. Upon dilution at a weight ratio of concentrate to liquid carrier of between about 1:2 and about 1:50, the desired wood preservative composition is provided.

The concentrate and the wood preservative compositions of the present invention may optionally include one or more co-biocides. Exemplary co-biocides are azoles such as one selected from cyproconazole, hexaconazole, difenaconazole, azaconazole, tebuconazole, propiconazole, and combinations thereof. Preferred azoles are tebuconazole, propiconazole, and combinations thereof. Other co-biocides can be used in these embodiment, such as thiocarbamates, isothiazolinones, thiocyanates, sulfenamides, quaternary phosphonium compounds, quaternary ammonium compounds and synergistic mixtures, and any other co-biocides that would be known to those skilled in the art. Exemplary other suitable co-biocides include but not limited to: (Thiocyanomethylthio)benzothiazole (TCMTB); Chlorothalonil; Dichlofluanid; Isothiazolone: 4,5-Dichloro-2-n-octyl-4-isothiazolin-3-one (DCOIT); 5-chloro-2-methyl-4-isothiazolin-3-one; 2-methyl-4-isothiazolin-3-one (MIT); Benzisothiazolin-3-one (BIT); 2-octyl-3-isothiazolone (OIT); Imidacloprid; Iodopropynyl Butylcarbamate (IPBC); Bifenthrin; Cypermethrin; Permethrin; Chitin; Chitosan; Clorpyrifos; 4-alpha-cumylphenol; Fipronil; Carbendazim; Cyfluthrin. The co-biocide, if used, is suitably employed in a weight ratio of between 1:1 and about 1:50 based upon the total weight of copper in the copper-based slurry.

In another embodiment, the present invention provides a stable wood preservative composition containing micronized copper, a liquid carrier, and a dispersing agent selected from the group consisting of a polycarboxylic acid or salt thereof; a lignosulfonic acid or salt thereof, and combinations thereof.

It is surprisingly found that these dispersing agents effectively prevent agglomeration of the micronized copper, thus greatly improving the stability of the micronized copper slurry. The liquid carriers which are used in the subject invention are those known in the art. The preferred lignosulfonic acid salt is lignosulfonic acid, sodium salt, sulfomethoxylated, supplied by Meadwestvaco under trade name Kraftsperse 25M.

As disclosed in US 2008/0011201, polycarboxylate dispersants are molecules or polymers that contain multiple carboxyl (COOH) groups which can form salts with metals and amine. Examples are styrene maleic anhydride copolymers in the form of their sodium or other alkali metal salts. Generally, excellent performance is achieved when the polycarboxylate dispersant is in the form of an addition copolymer. Suitable copolymers include salts of polyether polycarboxylates. These may be formed from acrylic acid and hydrophilic polyalkylene oxides such as polyethylene and polypropylene oxides. An example of such a copolymer is Ethacryl® G from Lyondell Chemie Nederland B.V. This is a polyether polycarboxylate, sodium salt supplied as a 40% aqueous solution. This copolymer is a comb-branched copolymer. The application publication, US 2008/0011201, is incorporated herein in its entirety.

The composition may further contain a copper-amine complex, a co-biocide, and combinations thereof. The copper-amine complex and the co-biocide are the same as those described above.

The following examples are intended to illustrate, but in no way limit the scope of the present invention. All parts and percentages are by weight and all temperatures are in degrees Celsius unless explicitly stated otherwise.

EXAMPLES

The micronized copper-based slurry preservative tested in accordance with the Examples herein described utilized a copper azole preservative system. The azole biocide comprised a mixture of tebuconazole and propiconazole, present in the slurry in a 1:1 weight ratio.

The micronized copper-based slurries were prepared by micronizing basic copper carbonate (BCC) from a single source using a commercial grinding apparatus, and adding dispersing agents to prevent agglomeration of the micronized particles. The dispersing agents used were: polyether polycarboxylate, sodium salt supplied by Lyondell Chemicals under trade name Ethacryl G and Lignosulfonic acid, sodium salt, sulfomethoxylated supplied by Meadwestvaco under trade name Kraftsperse 25M.

The micronized copper concentrate was prepared as follows: 1748 gm of basic copper carbonate was mixed with 951 gm water, 220 gm Ethacryl G, 92 gm Kraftsperse 25M and 3 gm Defomer. The mixture was mechanically stirred using a high speed mixture for 30 minutes. The mixture was then transferred into a Lab star grinding mill, supplied by Netzsch Laboratories, filled with 0.4-0.6 mm Zirstar grinding media for 90 minutes at 1200 rpm. The material was then analyzed for particle size using a CPS Disc centrifuge particle size analyzer. The particle size analysis results in microns are as follows

| 1% | 5% | 10% | 25% | 50% | 75% | 90% | 95% | 99% |
|---|---|---|---|---|---|---|---|---|
| 3.8049 | 0.8532 | 0.6896 | 0.5054 | 0.3596 | 0.2508 | 0.1732 | 0.1368 | 0.0943 |

After the BCC was micronized, the azole co-biocide was added and the slurry concentration adjusted with water to provide a copper azole preservative concentrate comprised of 33.3 percent copper. The particle size distribution of the micronized product was such that one percent of the particles had a particle size of 3.8049 microns or larger, and one percent had a particle size of 0.0943 micron or smaller, In order to model a formulated treatment composition, a mixture of isothiazolone moldicides were added to the diluted copper-based slurries. The moldicides were added to the diluted slurries in ppm levels. These moldicides are typically added to prevent mold growth on treated wood products at point of sale locations, as well as offer some initial protection against mold for the consumer of these products.

For the study, both a monoethanolamine complexed copper carbonate concentrate and monoethanolamine were trialed.

The complexed copper concentrate, containing 9.5 percent copper by weight, was comprised of a copper to monoethanolamine weight ratio of 1.0:3.4. This concentrate is designated as C-9. The monoethanolamine added to these slurries was assumed to be nearly 100 percent pure.

In order to examine a reasonable amount of wood surface area for chalk-like residues, six 2×6×24 inch southern yellow pine (SYP) boards were treated with micronized copper slurries containing the co-biocide and moldicides plus experimental additives in an attempt to reduce the chalk residues.

These boards were placed in a pilot plant wood treatment cylinder where an initial vacuum was applied (5 minutes at 22 inches of mercury), followed by pressure cycle (15 minutes at 150 psi), subsequent pressure reduction, followed by solution/slurry drains and finished with a final vacuum (30 minutes at 24-25 inches of mercury). This treatment cycle is typical of commercial treating cycles and was constant throughout the pilot plant study.

Example 1

Control Example with No Copper Amine

Control with No Anti-Chalk Additive

The copper slurry control was prepared by adding 272.7 grams of the micronized copper azole concentrate plus moldicides to water. The final weight of the wood treating solution was brought up to 100 pounds. The copper in this slurry was calculated to be 0.200 weight percent. The target copper retention expressed as pounds of copper per cubic foot (pcf) of wood is 0.050.

This solution was used to treat six 2×6×24 inch SYP boards as described above. For an average of the six boards, the initial board weight was 4.700 lbs and the final board weight was 7.826 lbs, leaving the weight gain associated with the treatment solution to be 3.126 lbs. The treating solution provided 27.28 lbs of weight per cubic foot ("pcf") of board, providing an amount of copper of 0.055 pcf.

FIGS. 1 and 2 illustrate the chalk-like deposits on the boards identified as Example #1 treated with the solution containing no residue control additive. Note the greenish residues at various locations in the photos.

Example 2

Addition of 10% C-9 Copper-MEA Concentrate to Micronized Copper

The copper slurry control was prepared by adding 245.4 grams of the micronized copper azole concentrate plus moldicides to water. To this mixture 94.58 grams of C-9 was added and the final weight of the wood treating solution was brought up to 100 pounds. The copper in this slurry was calculated to be 0.200 weight percent, 0.18 percent from the micronized copper and 0.02 percent from the C-9 concentrate. The resulting mixture contained 680 ppm of complexed/uncomplexed MEA. Again the target copper retention expressed as pounds of copper per cubic foot (pcf) of wood is 0.050.

This solution was used to treat six 2×6×24 inch SYP boards as described above. For an average of the six boards, the initial board weight was 4.125 lbs and the final board weight was 7.631 lbs, leaving the weight gain associated with the treatment solution to be 3.506 lbs. The treating solution provided 30.59 lbs of weight per cubic foot ("pcf") of board, providing an amount of copper of 0.061 pcf.

FIGS. 1 and 2 include photos taken of illustrative treated boards (identified as Example #2 on each of the Figures) show that no residue was observed when the C-9 additive was added at the 10 percent level, providing a total amount of monoethanolamine of 680 ppm.

Example 3

Addition of 20% C-9 Copper-MEA Concentrate to Micronized Copper

The copper slurry control was prepared by adding 218.1 grams of the micronized copper azole concentrate plus moldicides to water. To this mixture 189.0 grams of C-9 was added and the final weight of the wood treating solution was brought up to 100 pounds. The copper in this slurry was calculated to be 0.200 weight percent, 0.16 percent from the micronized copper and 0.04 percent from the C-9 concentrate. The resulting mixture contained 1360 ppm of complexed/uncomplexed MEA. Again the target copper retention expressed as pounds of copper per cubic foot (pcf) of wood is 0.050.

This solution was used to treat six 2×6×24 inch SYP boards as described above. For an average of the six boards, the initial board weight was 4.347 lbs and the final board weight was 7.696 lbs, leaving the weight gain associated with the treatment solution to be 3.349 lbs. The treating solution provided 29.22 lbs of weight per cubic foot ("pcf") of board, providing an amount of copper of 0.059 pcf.

FIGS. 1 and 2 include photos taken of illustrative treated boards (identified as Example #3 on each of the Figures) show that no residue was observed when the C-9 additive was added at the 20 percent level, thus providing a total amount of monoethanolamine of 1380 ppm.

Example 4

Addition of 34% Monoethanolamine to Micronized Copper in Order to Provide 10% Soluble Copper Based on the Total Weight of Copper in the Slurry The copper slurry control was prepared by adding 272.7 grams of the micronized copper azole concentrate plus moldicides to water. To this mixture 30.65 grams of MEA was added and the final weight of the wood treating solution was brought up to 100 pounds. The copper in this slurry was calculated to be 0.200 weight percent and the MEA at 675 ppm. Target copper retention expressed as pounds of copper per cubic foot (pcf) of wood is 0.050.

This solution was used to treat six 2×6×24 inch SYP boards as described above. For an average of the six boards, the initial board weight was 4.060 lbs and the final board weight was 7.720 lbs, leaving the weight gain associated with the treatment solution to be 3.660 lbs. The treating solution provided 31.94 lbs of weight per cubic foot ("pcf") of board, providing an amount of copper of 0.064 pcf.

FIGS. 1 and 2 include photos taken of illustrative treated boards (identified as Example #4 on each of the Figures). The photos taken of these treated boards show that no residue was observed when the MEA additive was added at the 34 percent level or 675 ppm of monoethanolamine.

Example 5

Addition of 68% Monoethanolamine to Micronized Copper in Order to Provide 20% of Soluble Copper Based on the Total Weight of Copper in the Slurry.

The copper slurry control was prepared by adding 272.7 grams of the micronized copper azole concentrate plus moldicides to water. To this mixture 61.30 grams of MEA was added and the final weight of the wood treating solution was brought up to 100 pounds. The copper in this slurry was calculated to be 0.200 weight percent and the MEA at 1350 ppm. Target copper retention expressed as pounds of copper per cubic foot (pcf) of wood is 0.050.

This solution was used to treat six 2×6×24 inch SYP boards as described above. For an average of the six boards, the initial board weight was 4.616 lbs and the final board weight was 7.148 lbs, leaving the weight gain associated with the treatment solution to be 2.532 lbs. The treating solution provided 22.10 lbs of weight per cubic foot ("pcf") of board, providing an amount of copper of 0.044 pcf.

FIGS. 1 and 2 include photos taken of illustrative treated boards (identified as Example #5 on each of the Figures). The photos taken of these treated boards show that no residue was observed when the MEA additive was added at the 68 percent level or 1350 ppm of monoethanolamine.

Example 6

Leach Testing Using Samples Made by Diluting the Micronized Copper Concentrate Having a Particle Size Distribution Described Herein Above The purpose of this test is to determine the leaching characteristics of Micro copper CA-C formulation using AWPA E11-06 standard method. This method provides an accelerated laboratory determination of the leachability of wood preservative expressed as a percentage of the original preservative retention.

Sample Preparation:

Blocks of wood measuring 19 mm (¾ in.) were pressure impregnated with the test preservative to obtain retentions of 0.05 pcf and 0.14 pcf for the micronized copper formulations and 0.06 pcf and 0.15 pcf for the Wolman CA-C (amine base) formulation. The followings are the formulations included for the leach test.
1) 0.05 pcf Microcopper CA-C (Control)
2) 0.14 pcf Micro copper CA-C (Control)
3) 0.05 pcf Micro copper CA-C+0.0475% MEA
4) 0.14 Pcf Micro copper CA-C+0.1360% MEA
5) 0.05 pcf Micro copper CA-C+0.0952% MEA
6) 0.14 Pcf Micro copper CA-C+0.272% MEA
7) 0.05 pcf Micro copper CA-C+0.238% MEA
8) 0.14 Pcf Micro copper CA-C+0.646% MEA
9) 0.06 pcf Wolman CA-C (copper amine control)
10) 0.15 pcf Wolman CA-C (copper amine control)

A total of nine blocks were treated for each treatment. The selection of blocks was done according to AWPA E11 with the density range kept as narrow as possible. Blocks were numbered and weighed to the nearest of 0.01 g before and after treatment to obtain the solution retention. Following treatment, each block was removed from the solution, wiped lightly to remove the surface deposits and weighed immediately to the nearest 0.01 g. The blocks were then put in a plastic bag for one week followed by two days of air drying at room temperature. Prior to the leach test, the blocks were condition in a chamber for three weeks. The conditioning chamber was maintained at 23±0.5° C. and 50±2% relative humidity.

Leaching Procedure:

From each treatment 6 blocks were selected for leach test and 3 kept for analysis to determine the unleached retention level. One set of leach tests were set up for each treatment using six blocks per test. Prior to leaching, blocks were impregnated with 300 ml of 4-stage deionized (DI) water. After impregnation, the water level was adjusted back to the total volume of 300 ml by adding DI water. The water was stirred using a magnetic stir bar of the same size for all containers. The blocks were kept fully submerged in the water for the duration of the test. The beakers containing the blocks were covered with aluminum foil to prevent evaporation of the leachate. The temperature of the room was maintained at 23±0.5° C. during testing. The leachate water was changed with an equal amount of fresh DI water after 6, 30, 78, 166, 238 and 310 hours.

Analysis:

After completing the leach test, leachate samples for each formulation was analyzed for elemental copper using Inductively Coupled Plasma Emission Spectrometry (ICP).

Results:

Attached is the table showing the % copper loss results over time for individual treatment.

TABLE 1

Leach Test Results
AWPA E-11-06 Leach Test

| Cumulative Hours | 6 | 30 | 78 | 166 | 238 | 310 | Totals |
|---|---|---|---|---|---|---|---|
| 0.05 pcf MCA-C (CONTROL) | | | | | | | |
| Cu (mg/l) | 1.719 | 1.407 | 1.078 | 1.371 | 0.847 | 0.645 | 7.067 |
| % loss | 1.854 | 1.517 | 0.996 | 1.267 | 0.782 | 0.596 | 7.012 |
| 0.14 pcf MCA-C (CONTROL) | | | | | | | |
| Cu (mg/l) | 3.211 | 2.458 | 1.987 | 2.510 | 1.529 | 1.123 | 12.818 |
| % loss | 1.195 | 0.914 | 0.634 | 0.800 | 0.488 | 0.358 | 4.389 |
| 0.05 pcf MCA-C + 0.0475 % MEA | | | | | | | |
| Cu (mg/l) | 1.243 | 0.948 | 0.707 | 0.879 | 0.510 | 0.373 | 4.660 |
| %loss | 1.337 | 1.019 | 0.652 | 0.811 | 0.470 | 0.344 | 4.632 |
| 0.14 pcf MCA-C + 0.136 % MEA | | | | | | | |
| Cu (mg/l) | 1.348 | 1.124 | 1.116 | 1.286 | 0.813 | 0.638 | 6.325 |
| % loss | 0.512 | 0.427 | 0.363 | 0.419 | 0.265 | 0.208 | 2.194 |
| 0.05 pcf MCA-C + 0.0952 % MEA | | | | | | | |
| Cu (mg/l) | 1.182 | 0.938 | 0.746 | 0.953 | 0.543 | 0.381 | 4.742 |
| % loss | 1.286 | 1.020 | 0.696 | 0.888 | 0.506 | 0.356 | 4.753 |

TABLE 1-continued

Leach Test Results
AWPA E-11-06 Leach Test

| Cumulative Hours | 6 | 30 | 78 | 166 | 238 | 310 | Totals |
|---|---|---|---|---|---|---|---|
| 0.14 pcf MCA-C + 0.272 % MEA | | | | | | | |
| Cu (mg/l) | 1.473 | 1.231 | 1.158 | 1.503 | 1.269 | 0.903 | 7.538 |
| % loss | 0.554 | 0.462 | 0.373 | 0.484 | 0.409 | 0.291 | 2.573 |
| 0.05 pcf MCA-C + 0.238 % MEA | | | | | | | |
| Cu (mg/l) | 0.949 | 0.613 | 0.439 | 0.488 | 0.294 | 0.229 | 3.012 |
| % loss | 0.724 | 0.468 | 0.287 | 0.320 | 0.192 | 0.150 | 2.142 |
| 0.14 pcf MCA-C + 0.646 % MEA | | | | | | | |
| Cu (mg/l) | 2.473 | 1.745 | 1.340 | 1.476 | 1.013 | 0.760 | 8.808 |
| % loss | 0.958 | 0.676 | 0.445 | 0.490 | 0.336 | 0.252 | 3.157 |
| 0.06 pcf CA-C (copper amine control) | | | | | | | |
| Cu (mg/l) | 2.768 | 1.826 | 1.296 | 1.264 | 0.543 | 0.315 | 8.013 |
| % loss | 2.456 | 1.620 | 0.986 | 0.961 | 0.413 | 0.240 | 6.676 |
| 0.15 pcf CA-C (copper amine control) | | | | | | | |
| Cu (mg/l) | 12.242 | 7.436 | 4.377 | 4.253 | 1.876 | 1.083 | 31.267 |
| % loss | 4.203 | 2.553 | 1.288 | 1.252 | 0.552 | 0.319 | 10.166 |

The results shown in Table 1 indicate that significant copper loss was found for the Control Example using micronized copper without copper amine. Likewise, significant copper loss was found for the Control Example using copper amine without micronized copper. In contrast, the loss of copper from wood due to leaching was substantially less for test runs using various combinations of micronized copper plus copper amine as shown in Table 1. A graphical depiction of the leach rate differences for samples tested is provided in FIGS. 3 and 4. These graphs represent the cumulative leach results of micronized copper with and without MEA in the formulation over the 310 hour leach period. A copper amine formula was also included in the test for comparison. Retention levels were those recommended by the chemical supplier for the respective preservative and use application. As shown in the FIG. 3, the 0.06 pcf copper amine and the 0.05 pcf micro copper system have the highest leach rate. Micronized copper blended with MEA shows a significant reduction in copper leaching at all tested levels. This was a surprising test result. This finding was also supported by the higher retention (0.14 pcf) leach test data. As shown in FIG. 4, 0.15 pcf copper amine system had the highest leach rate as expected followed by micro copper only formulation. Again, the micro copper with MEA addition showed significant leach reduction compared to micro copper and copper amine systems.

What is claimed is:

1. An improved method for reducing chalking on the surface of treated wood, the improvement comprising treating wood with a composition comprising micronized copper and a copper-amine complex, wherein the copper component of the copper amine complex is from about 5% to about 25% by weight, based upon the total weight of copper in the composition, the amine of the copper-amine complex is selected from the group consisting of monoethanolamine, diethanolamine, and combinations thereof, and the weight ratio of copper to amine in the copper-amine complex is between 1.0:3.3 and 1.0:3.5.

2. The method of claim 1, wherein the composition additionally comprises an organic co-biocide.

3. The method of claim 2, wherein the organic co-biocide is an azole.

4. The method of claim 3, wherein the azole is selected from the group consisting of hexaconazole, difenaconazole, azaconazole, tebuconazole, propiconazole, and combinations thereof.

5. The method of claim 1, wherein the micronized copper is selected from the group consisting of elemental copper, copper carbonates, copper oxides, copper hydroxides, copper chlorides, copper aromatic or aliphatic carboxylates, and copper aminocarboxylates, and combinations thereof.

* * * * *